United States Patent [19]

Frantzich et al.

[11] Patent Number: 4,934,357
[45] Date of Patent: Jun. 19, 1990

[54] JAW SUPPORT BANDAGE

[76] Inventors: William P. Frantzich; Saundra L. Frantzich; Paul E. Frantzich, all of 2660 Stone Arch Rd., Wayzata, Minn. 55391

[21] Appl. No.: 220,179

[22] Filed: Jul. 18, 1988

[51] Int. Cl.[5] ............................................. A61F 13/12
[52] U.S. Cl. .................................................... 128/164
[58] Field of Search ................. 128/76 R, 76 B, 380, 128/399, 857, 869, DIG. 15, 848, 162-164, 402, 403; 272/119, 94, 95; 433/5

[56] References Cited

U.S. PATENT DOCUMENTS

| | | | |
|---|---|---|---|
| 955,562 | 4/1910 | Thomas | 128/164 |
| 1,216,679 | 2/1917 | Foster | 128/164 |
| 1,247,222 | 11/1917 | Cauffman | 128/164 |
| 1,296,946 | 3/1919 | Galiardo | 128/848 X |
| 3,491,761 | 1/1970 | Baker | 128/402 |
| 3,572,329 | 3/1971 | De Woskin | 128/164 X |
| 3,709,225 | 1/1973 | Sobel | 128/164 X |
| 4,190,054 | 2/1980 | Brennan | 128/163 X |
| 4,585,003 | 4/1986 | Meistrell | 128/402 |
| 4,658,811 | 4/1987 | Beaird | 128/163 |

FOREIGN PATENT DOCUMENTS

| | | | |
|---|---|---|---|
| 430231 | 6/1935 | United Kingdom | 128/164 |
| 520600 | 4/1940 | United Kingdom | 128/164 |

Primary Examiner—Richard J. Apley
Assistant Examiner—D. F. Crosby

[57] ABSTRACT

A jaw support bandage includes a jaw support body comprised of a jaw and chin engaging portion and cheek and temporal engaging portions. First and second pairs of mating straps extend from the jaw support body, and each strap is provided with a quick release type fastener on its outer end for attachment to its associated mating strap. When the jaw support bandage is applied to the head of a patient, the mating interconnected straps are spaced from each other a predetermined distance to prevent slippage of the bandage from the patient's head. In one embodiment of the invention, the mating interconnected straps extend over the coronal portion of the patient's head. In another embodiment of the invention, one mating pair of straps extends over the coronal portion of the patient's head and the other mating pair of straps extends around the forehead and rear portion of the patient's head.

1 Claim, 2 Drawing Sheets

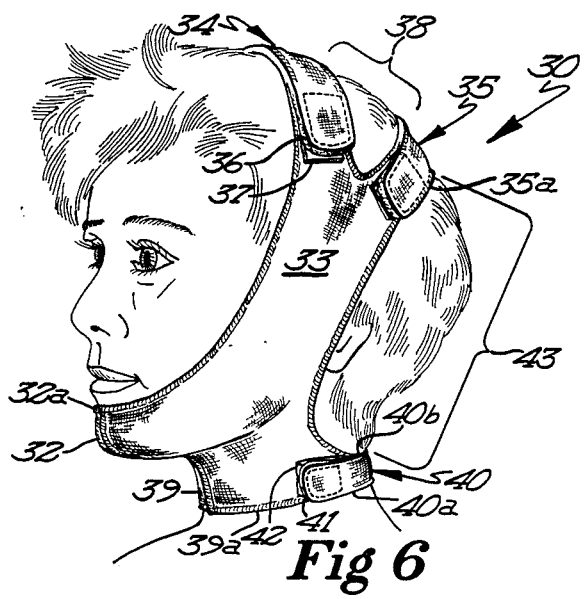
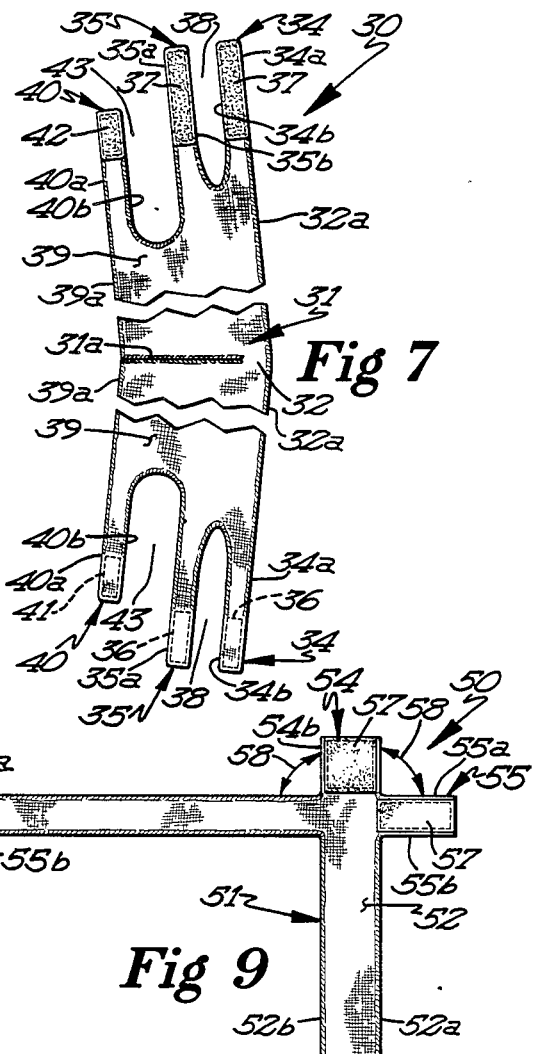
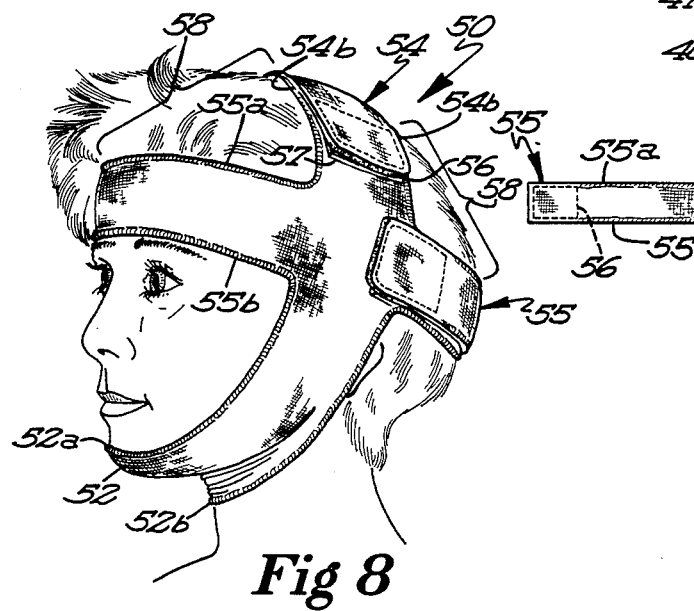
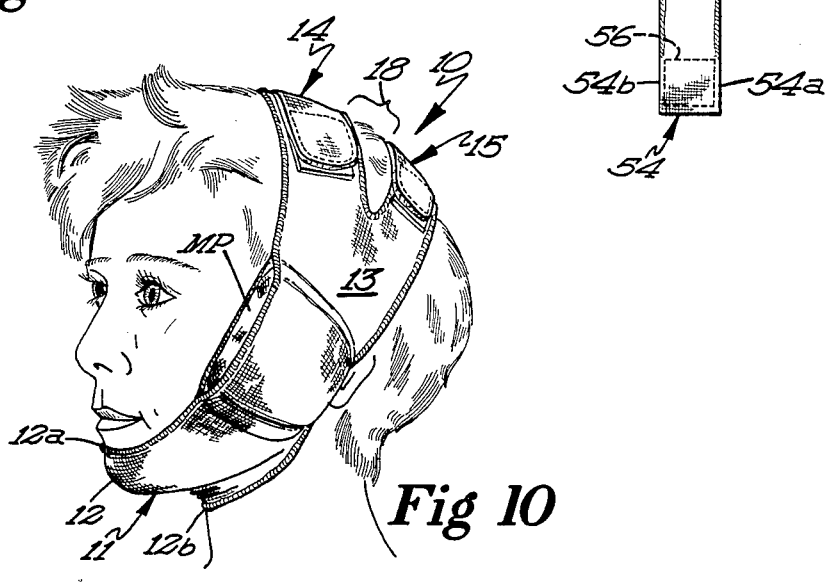

JAW SUPPORT BANDAGE

This invention relates to a jaw support bandage for providing support to the jaw of a person.

SUMMARY OF THE INVENTION

An object of this invention is to provide a highly stable jaw support bandage for providing support to the jaw of a patient after oral surgery or the like.

Another object of this invention is to provide a flexible jaw support bandage for patients, which may be readily applied to and readily removed from the patient with a minimum of effort and in a minimum amount of time.

A further object of this invention is to provide a flexible jaw support bandage, of simple and inexpensive construction, which includes a jaw support body having mating interconnectable pairs of straps extending therefrom, the mating straps, when interconnected, defining a space therebetween, which is of a magnitude to stabilize the bandage against slipping with respect to the patient's head.

In carrying out this invention, the novel jaw support bandage includes a flexible jaw support body, which engages the lower surface of the jaw, chin, cheek, neck, and temporal portions of the patient's head for providing support thereto. The jaw support body is provided with two pairs of mating straps that extend around portions of the patient's head. The ends of the straps are provided with readily attachable and detachable Velcro-type fasteners or the like, which permits easy and quick application of the jaw support bandage to the patient's head. The spacing between the mating pairs of straps is of a magnitude to provide stability to the jaw support bandage and reduce the likelihood of slippage of the bandage from the patient's head.

These and other objects will be more fully defined in the following Specification.

FIGURES OF THE DRAWING

FIG. 6 is a perspective view of another embodiment of the novel jaw support bandage applied to the head of a patient;

FIG. 7 is a plan view of the jaw support bandage illustrated in FIG. 6 and foreshortened for clarity;

FIG. 8 is a perspective view of a further embodiment of the novel jaw support bandage applied to the head of a patient;

FIG. 9 is a plan view of the jaw support bandage illustrated in FIG. 8; and

FIG. 10 is a perspective view of the jaw support bandage illustrated in FIG. 1, but further showing the use of a medicated pad used in conjunction with the jaw support bandage.

DESCRIPTION OF THE PREFERRED EMBODIMENT

Figure 1:
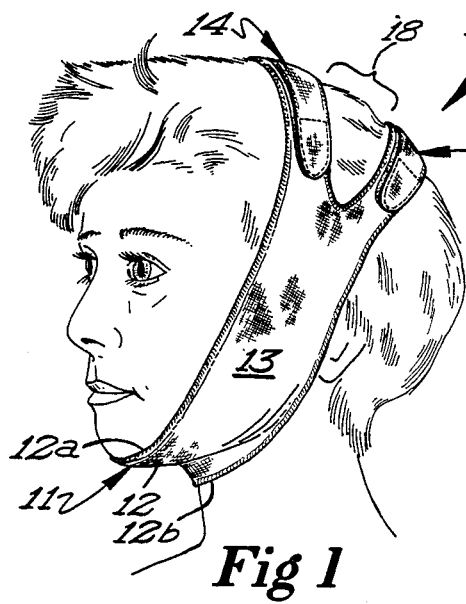
FIG. 1 is a perspective view of one embodiment of the novel jaw support bandage applied to the head of a patient.
Figure 2:
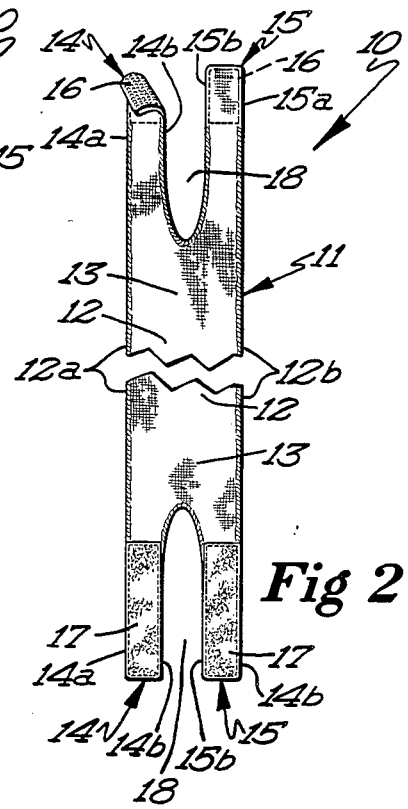
FIG. 2 is a plan view of the novel jaw support bandage illustrated in FIG. 1, foreshortened for clarity and with an end portion of a strap turned up to illustrate the fastening means utilized thereon.

Referring now to the drawings and, more specifically, to FIGS. 1 and 2, it will be seen that one embodiment of the novel jaw support bandage, designated generally by the reference numeral 10, is thereshown. The jaw support bandage 10 is of single-piece construction and may be formed of a suitable flexible somewhat elastic material. The jaw support bandage is applied to a patient's head following surgery or injury to the jaw region of the patient. although jaw support bandages are used to provide support to a patient's jaw region, such bandages are usually applied by wrapping a length of bandage around the patient's head in supporting relation with respect to the jaw.

Applicant's jaw support bandage may be formed from a single generally rectangular piece of material and includes a jaw support body 11, which engages the jaw, chin, cheek, neck, and temporal portions of the patient. The jaw support body 11 includes a jaw and chin engaging portion 12 which engages the lower surface of the jaw, as well as a portion of the chin and neck of the patient. The jaw support body 11 also includes cheek and temporal engaging portions 13, which are integral with the jaw and chin engaging portions, and which extend upwardly therefrom. It will be seen that the jaw and chin engaging portion 12 has a front edge 12a and a rear edge 12b that is coextensive with the respective front and rear edges of the cheek and temporal portions 13.

The jaw support body 11 has integrally formed therewith a first pair of elongate mating coronal straps 14 and one of a second pair of elongate mating coronal straps 15. The end portion of one of the coronal straps 14 has Velco loops integrally formed on one surface thereof, and the end portion of the other coronal strap 14 has Velcro hooks on one surface thereof. Similarly, the end portions of the second pair of mating coronal straps 15 are provided with Velcro loops 16 and Velcro hooks 17. It will be noted that the mating pairs of straps are of a length to overlap each other to thereby permit the Velcro loops and hooks to be releasably secured together. It is pointed out that fastening means, other than Velcro fastening means, may be employed to releasably secure the end portions of the mating straps together.

Each of the coronal straps 14 has an outer edge 14a, which is substantially coextensive with the front edge 12a of the jaw support body 11. Similarly, each of the second pair of straps 15 has an outer edge 15a, which is coextensive with the outer edge of the jaw support body 11. Each of the coronal straps 14 also has an inner edge 14b, while each of the coronal straps 15 has an inner edge 15b. It will be noted that the inner edges of the mating straps are spaced apart when the jaw support bandage 10 is applied to the head of a patient. The spacing 18 between the inner edges of the interconnected mating coronal straps are important in providing stability to the jaw support bandage against slippage when the latter is applied to the head of a patient.

It has been found that the spacing between the interconnected mating coronal straps should be within the range of ½ inch to 8 inches in order to provide the necessary stability against slippage. The dimension of the spacing 18 between the central portion of the interconnected mating coronal straps 14 and 15 is approximately 3 inches. The quick fastening means for the coronal straps permits jaw support bandage 10 to be readily applied to and removed from the head of a patient with a minimum of effort.

Figure 3:
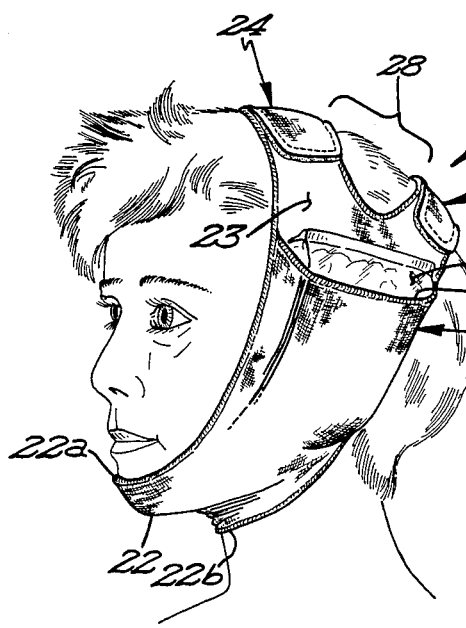
FIG. 3 is a perspective view of a different embodiment of the novel jaw support applied to the head of a patient.
Figure 4:
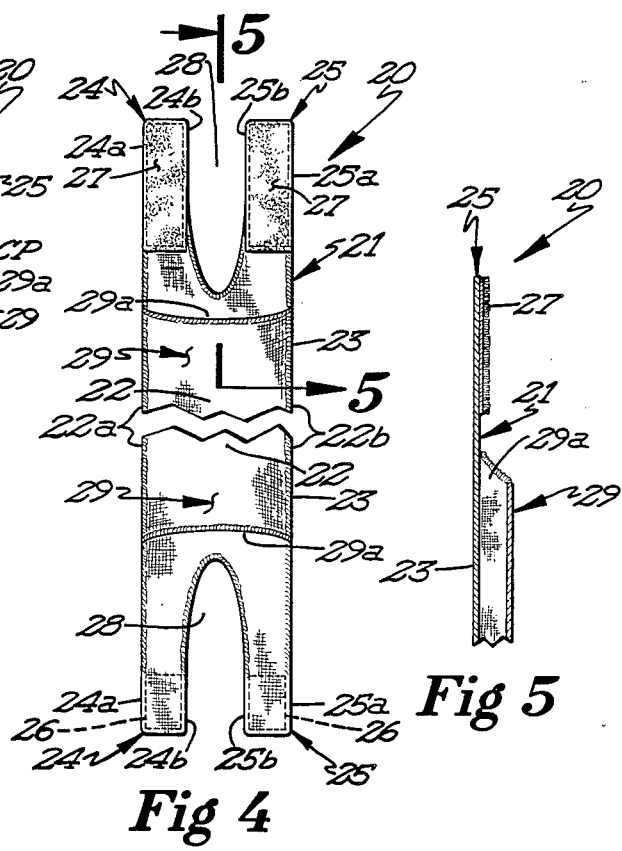
FIG. 4 is a plan view of the jaw support bandage illustrated in FIG. 3 and foreshortened for clarity.
Figure 5:
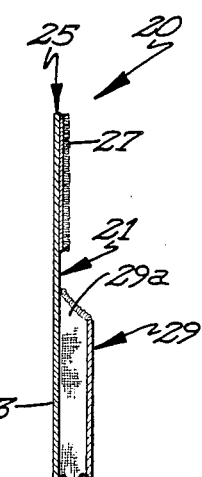
FIG. 5 is a cross-sectional view taken approximately along the line 5—5 of FIG. 4 and looking in the direction of the arrows.

Referring now to FIGS. 3-5, it will be seen that a different embodiment of the jaw support bandage, designated generally by the reference numeral 20, is thereshown. The jaw support bandage 20 also includes a jaw support body 21 comprised of a jaw and chin engaging portion 22 and cheek and temporal engaging portions 23. The jaw support bandage 20 also includes a first pair of mating coronal straps 24 and a second pair of mating coronal straps 25, which are integral with the jaw support body 11. The end portions of the mating pairs of coronal straps are provided with cooperating Velcro loops 26 and Velcro hooks 27, in the manner of the embodiment of FIGS. 1 and 2.

It will be noted that, when the jaw support bandage 20 is applied to a patient's head, the dimension of the spacing 28 between the interconnected mating pairs of coronal straps 24 and 25 is of a magnitude to preclude slippage of the jaw support bandage from the patient's head. In the embodiment shown, the spacing 28 is approximately 3 inches between the mid-portions of the interconnected coronal straps 24 and 25.

The jaw support body 21 has a substantially straight front edge 22a, which is substantially coextensive with the outer edges 24a of the coronal straps 24. Similarly, the jaw support body 21 has a rear edge 22b which is substantially coextensive with the outer edges 25a of the coronal straps 25 The coronal straps 24 have inner edges 24b, while the coronal straps 25 have outer edges 25b spaced from the inner edges 24b of the coronal straps 24.

The jaw support bandage 20 is provided with a panel 29, which is fixed or otherwise secured to the jaw support body 21 for a major portion of the length of the latter. The pocket 29a can accommodate a chill pack CP therein to provide cooling of the patient's jaw or cheek area, as required. In this regard, a pair of chill packs may be provided for each jaw or cheek, when necessary or desired.

Referring now to FIGS. 6 and 7, it will be seen that another embodiment of the novel jaw support bandage, designated generally by the reference numeral 30, is thereshown. This jaw support bandage 30 is also formed from a single piece of flexible elastic material and includes a jaw support body 31, which is comprised of a jaw and chin engaging portion 32 and cheek and temporal engaging portions 33. The jaw support body 31 is provided with a first pair of mating coronal straps 34 and a second pair of coronal straps 35, which extend from the cheek and temporal engaging portions. The end portions of the mating pairs of coronal straps are provided with Velcro fastening loops 36 and Velcro hooks 37.

It will be noted that the jaw support body has a front edge 32a, which is substantially coextensive with the outer edges 34a of the coronal straps 34. It will further be noted that the coronal straps 34 each have an inner edge 34b which is spaced from the inner edge 35b of each cf the second pair of coronal straps. With this arrangement, when the jaw support bandage is applied to a patient's head, the respective inner edges of the mating interconnected straps 34 and 35 will be spaced apart from each other, and the dimension of this spacing 38 corresponds to the dimension of the spacings between the interconnected mating straps of the embodiments of FIGS. 1-5.

It will also be noted that the jaw support bandage 30 also includes a neck engaging portion 39, which engages the front or ventral portion of a person's neck and extends around a major part thereof. In order to provide the proper configuration to the neck engaging portion 39 and the jaw support body, the rectangular blank is cut transversely adjacent the central portion thereof and is resewn together to form a seam 31b, as best seen in FIG. 7.

The jaw support bandage 30 is also provided with a pair of neck engaging mating straps 40, which are integral with the neck engaging portion 39, and which extend outwardly therefrom. The end portions of the mating straps 40 are provided with cooperating Velcro loops 41 and Velcro hooks 42, as best seen in FIG. 7.

The neck engaging straps 40 each have an outer edge 40a, which is disposed in substantially coextensive relation with respect to the lower edge 39a of the neck engaging portion 39. Each of the neck engaging straps 40 has an inner or upper edge 40b, which is spaced from the outer edge 35a of the second pair of coronal straps 35 when the jaw support bandage is applied to a patient's head. In the embodiment shown, this spacing 43 from the center of the interconnected neck straps to the center of the second pair of interconnected coronal straps 35 is approximately 6 inches. The spacing between the mid-portions of the interconnected straps 34 and the interconnected coronal straps 35 is approximately 3 inches. This spacing, of course, stabilizes the jaw support bandage against movement. The neck support portion 39 provides additional support to the neck of the patient, which is required in certain types of oral surgery or injury.

Referring now to FIGS. 8 and 9, it will be seen that another embodiment of the novel jaw support bandage, designated generally by the reference numeral 50, is thereshown. The jaw support bandage 50 includes a jaw support body 51, which is comprised of a jaw and chin engaging portion 52 and cheek and temporal portions 53. The jaw support body 51 has a first pair of mating coronal straps 54 integrally formed therewith and extending outwardly therefrom, as best seen in FIG. 9.

In this regard, it will be noted that the width of the jaw support body 51 is the same as the width of the first pair of straps 54. The straps 54 are coextensive with the jaw support body 51. One of the straps 54 has a length dimension substantially shorter than the length dimension of the other strap 54. The front edge 54a and the rear edge 54b of the coronal straps 54 are coextensive, respectively, with the front and rear edges of the jaw support body 51.

A second pair of straps 55 is integrally formed with the jaw support body 51 and extends therefrom and at substantially right angular relationship therewith, as best seen in FIG. 9. These straps 55 also have an upper edge 55a and a lower edge 55b and extend around the forehead and rear portion of the patient's head. It will be noted that one of the straps 55 has a length dimension substantially shorter than the length dimension of the other strap 55. Velcro loop fasteners 56 and Velcro hook fasteners 57 are secured to ends of the mating pairs of straps 54 and the mating pairs of straps 55.

It will be seen that, when the jaw support bandage 50 is applied to the head of a patient, the jaw support body 51 will underlie and engage the jaw, chin, cheek, and temporal portions of the patient's head, as well as a small portion of the neck. The straps 54 will extend over the coronal portion of the patient's head in overlapping relation with respect to each other, and the straps 55 will extend around the forehead and rear portion of the patient's head. The spacing between the front edge 54a of the mating interconnected straps 54 and the upper edge 55a of the straps 55 defines a space 58. A space 58 of the same magnitude is defined rearwardly of the mating coronal straps 54 and the mating straps 55. The dimensions of the spacings 58 between the interconnected central portion of the coronal straps 54 and the central portions of the mating straps 55 are approximately 3½ inches. Again, it is pointed out that this spacing provides stability and prevents slippage of the bandage from the patient's head.

FIG. 10 is an illustration of the jaw support bandage 10 of FIG. 1 and is illustrated in conjunction with a medicated pad MP. The medicated bandage is inserted between the cheek and temporal portion of the bandage and the cheek and temporal areas of the patient. It is pointed out that medicated pads can be applied to both sides of the face of the patient.

From the foregoing, it will be seen that the novel jaw support bandage is not only highly effective in providing the necessary support to a patient's jaw, but this novel jaw support bandage may be quickly and easily applied to a patient.

Thus, it will be seen that this novel jaw support bandage is not only of simple and inexpensive construction, but is one which functions in a more efficient manner than any heretofore known comparable bandage.

WHAT IS CLAIMED IS:

1. A flexible single-piece jaw support bandage formed from a single rectangular piece of flexible elastic material for providing support to the jaw of a patient after oral surgery or the like, comprising:

an imperforate jaw support body having front and rear longitudinal edges and including a jaw and chin engaging portion having width and length dimensions of a magnitude for use in engaging, supporting, and covering the lower surface of the jaw, a portion of the chin, and the front portion of the neck of a patient, said jaw support portion including a pair of cheek and temporal engaging portions integral with said jaw and chin engaging portions and having width and length dimensions of a magnitude for use in engaging and covering the cheeks and temporal areas of a patient, said jaw support body having inner and outer surfaces, the inner surface of said jaw support body adapted for being positioned directly against the neck, chin, cheeks and temporal areas of a patient, and first and second pairs of straps integral with the cheek and temporal engaging portions and said jaw support body and extending therefrom, each strap of a mating pair being of a length for use in extending over the coronal portion of the patient's head to overlap the end portion of the associated mating strap, said straps having the same length dimension and having substantially uniform width dimensions, one strap of each pair having a front longitudinal edge extending coextensively with the front longitudinal edge of said jaw support body, the other strap of each pair having a rear longitudinal edge extended coextensively with the rear longitudinal edge of the jaw support body, and cooperating ready attachable and releasable fastening means on the end portions of mating straps to permit the end portions of a mating pair of straps to be readily secured together and to be readily detached from each other, the interconnected straps of one mating pair being spaced apart from the interconnected straps of the other mating pair, said spacing between said interconnected mating pairs of straps being within the range of approximately 178 inch to 8 inches to prevent slippage of the jaw support bandage from the patient's head, and a pocket defining an elongate, rectangular-shaped, imperforate flexible panel having longitudinal and end edges, the longitudinal edges of said panel being secured to the longitudinal edges of the jaw support body throughout a major portion of the length dimension of the latter, the end edges of said panel being located adjacent the temporal engaging portions of said jaw support body, and said panel cooperating with said jaw support body to define an elongate pocket having opposite ends thereof open and facing upwardly when the bandage is applied to a patient's head for accommodating cooling packs and the like.

* * * * *